(12) United States Patent
Chau et al.

(10) Patent No.: US 7,511,820 B2
(45) Date of Patent: Mar. 31, 2009

(54) SURFACE PLASMON RESONANCE SENSING SYSTEM AND METHOD THEREOF

(75) Inventors: Lai-Kwan Chau, Chiayi (TW); Wei-Ting Hsu, Jhonghe (TW); Shu-Fang Cheng, Chiayi (TW)

(73) Assignee: National Chung Cheng University, Chia-Yi (TW)

( * ) Notice: Subject to any disclaimer, the term of this patent is extended or adjusted under 35 U.S.C. 154(b) by 0 days.

(21) Appl. No.: 11/558,868

(22) Filed: Nov. 10, 2006

(65) Prior Publication Data

US 2007/0109545 A1   May 17, 2007

(30) Foreign Application Priority Data

Nov. 11, 2005   (TW)   ................. 94139665 A

(51) Int. Cl.
*G01N 21/55* (2006.01)

(52) U.S. Cl. ...................................... 356/445

(58) Field of Classification Search .................. None
See application file for complete search history.

(56) References Cited

U.S. PATENT DOCUMENTS

2005/0186565 A1 *   8/2005   Malak .................. 435/5
2006/0197952 A1 *   9/2006   Chen et al. ............. 356/445

* cited by examiner

*Primary Examiner*—Michael P Stafira
(74) *Attorney, Agent, or Firm*—WPAT, P.C.; Anthony King

(57) ABSTRACT

A surface plasmon resonance sensing system and method thereof are disclosed. The system comprises an incident light source, a sensing element, a noble metal nanoparticle layer, a sample loading unit, and a light detector. The noble metal nanoparticle layer is composed of one of noble metal nanoballs, noble metal nanorods and noble metal nanoshells. The noble metal nanoparticle layer is disposed on the sensing element. The sample loading unit is used to allow a sample to be contacted with the noble metal nanoparticle layer. The light detector is used to detect an emergent light of the sensing element.

9 Claims, 3 Drawing Sheets

US 7,511,820 B2

SURFACE PLASMON RESONANCE SENSING SYSTEM AND METHOD THEREOF

FIELD OF THE INVENTION

The present invention relates to a surface plasmon resonance sensing system and method thereof, and more particularly to use one of a noble metal nanosphere, a noble metal nanorod and a noble metal nanoshell to be a nano material.

BACKGROUND OF THE INVENTION

Surface plasmon resonance phenomenon is that when a light source illuminates a metal surface at a fixed incident angle, the reflection intensity detected by a light detector would be near zero, which means the reflectivity of the metal film is near zero. The light which is not reflected will propagate along interface direction at a certain velocity to resonantly excite the surface plasmon of the metal. The method of measuring the reflected light is known as Attenuated Total Reflection (ATR).

A surface plasmon resonance sensing system uses a sensing system made by surface plasmon resonance phenomenon. Because the surface plasmon resonance sensor has high sensitivity, is label-free for detecting molecules, and can analyze the interaction between molecules at real-time. Other advantages include short analysis time and capability of simultaneous parallel detection. The system is therefore in widespread use on detecting biomolecules.

Recently, the development of nanomaterials is applied to optoelectronics, communication and medical equipment. Nanomaterials may provide specific characteristics which completely differ from traditional materials. The localized surface plasmon resonance (LSPR) associated with gold nanoparticles is utilized to replace propagating surface plasmon resonance (PSPR) associated with traditional gold thin film. The sensitivity of the sensor is still good and other features such as pixel size and simplicity in construction of the sensor are then improved. The approach of synthesizing nanoparticles has chemical and physical ways. The physical way includes metal vapor deposition, laser ablation, and sputtering, wherein the metal vapor deposition is frequently used. The chemical way includes reduction method and electrolysis method. The reduction method is frequently used, and is also the most important way. However, when the technology is increasingly developed, the sensitivity of the sensor needs to be further improved.

To further improve the sensitivity of the sensing system, the inventor of the present invention based on years of experience to conduct extensive researches and experiments invents a surface plasmon resonance sensing system and method thereof, as a method or a basis for achieving the aforementioned object.

SUMMARY OF THE INVENTION

Accordingly, a primary object of the present invention is to provide a surface plasmon resonance sensing system and method thereof that provide one of noble metal nanospheres, noble metal nanorods and noble metal nanoshells to be a nanomaterial so as to achieve the goal of improving the sensitivity and other performance criteria of the surface plasmon resonance sensing system.

To achieve the foregoing object, the surface plasmon resonance sensing system according to the invention comprises an incident light source, a sensing element, a noble metal nanoparticle layer, a sample loading unit and a light detector. The sensing element is an optical fiber where a portion of the protection layer and the cladding layer are removed or a planar waveguide plate. The noble metal nanoparticle layer is composed of one of the noble metal nanospheres, the noble metal nanorods and the noble metal nanoshells, and is disposed onto the surface of the sensing element. The sample loading unit is used to allow a sample to be contacted with the noble metal nanoparticle layer. The light detector is used to detect an emergent light of the sensing element.

Other features and advantages of the present invention and variations thereof will become apparent from the following description, drawings, and claims.

DETAILED DESCRIPTION OF THE PREFERRED EMBODIMENTS

Figure 1:
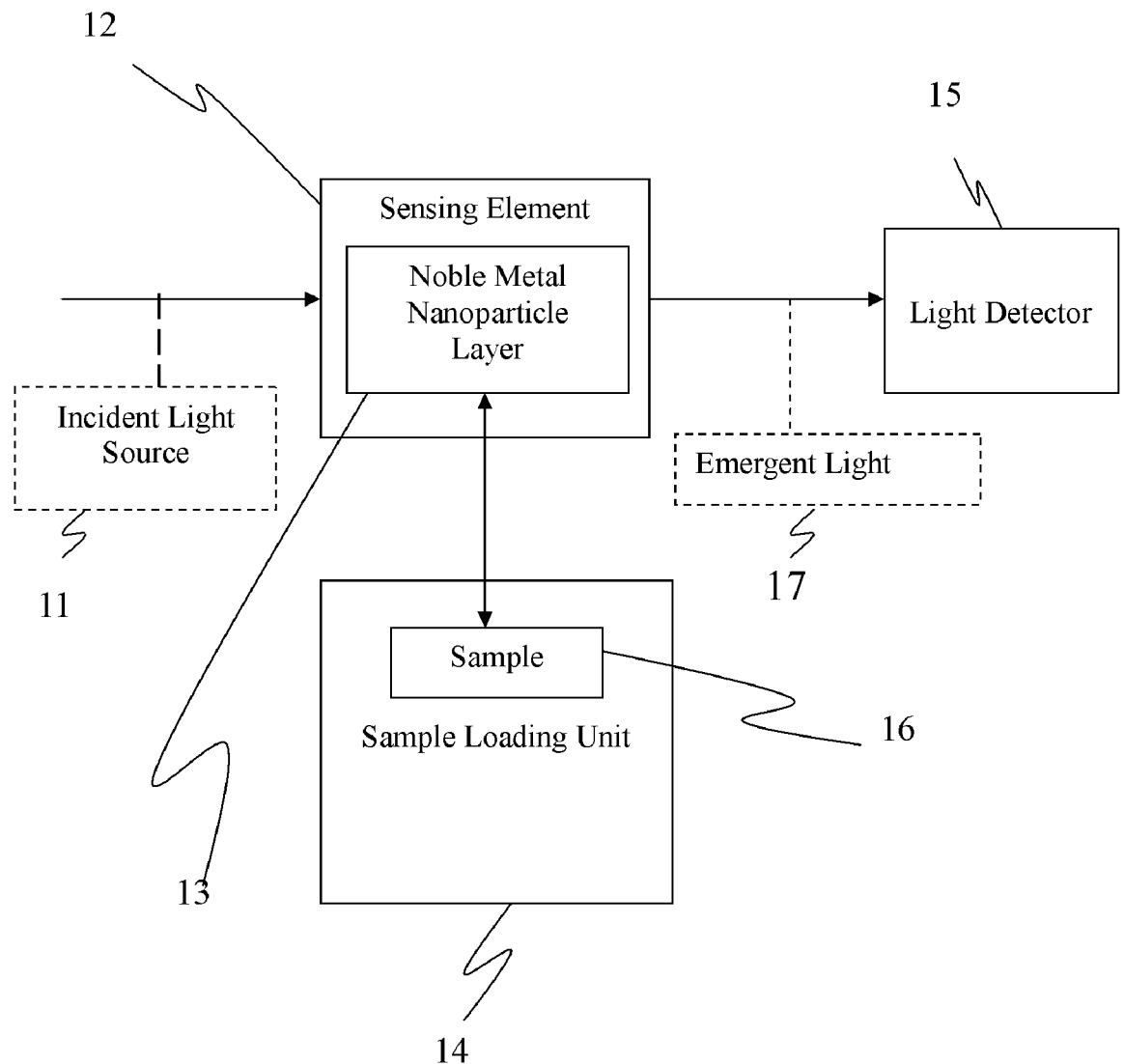
FIG. 1 is a block diagram illustrating a surface plasmon resonance sensing system of the present invention.

Referring to FIG. 1, a block diagram illustrates a surface plasmon resonance sensing system according to an embodiment of the present invention. The surface plasmon resonance sensing system comprises an incident light source 11, a sensing element 12, a noble metal nanoparticle layer 13, a sample loading unit 14 and a light detector 15. The incident light source 11 is a single frequency light, a narrow frequency band light or a white light. The sensing element 12 is an optical fiber where a portion of the protection layer and the cladding layer are removed or a planar waveguide plate. The noble metal nanoparticle layer 13 is composed of one of noble metal nanospheres, noble metal nanorods and noble metal nanoshells, and is disposed onto the surface of the sensing element 12. The sample loading unit 14 allows a material 16 to be contacted with the noble metal nanoparticle layer 13. The light detector 15 is used to detect an emergent light 17 of the sensing element. The emergent light is a transmitted light, a reflected light, or a leaked light from an unclad portion of the optical fiber or from the planar waveguide plate.

The noble metal comprises gold, silver or platinum. The nanoparticles have different specific characteristics based on different shapes. In the invention, the deviation of the maximum wavelength absorption generated by per refractive index unit (RIU) of the gold nanorod is 366.0 nm (nanometer)/RIU. The deviation of the maximum wavelength absorption generated by per refractive index unit (RIU) of the gold nanoshell is 222.8 nm/RIU. The deviation of the maximum wavelength absorption generated by per refractive index unit (RIU) of the gold nanosphere is 77.2 nm/RIU.

Accordingly, the sensitivity of the surface plasmon resonance sensing system composed of nanoparticles with different shapes also has obvious differences.

Furthermore, to compare with other nanomaterials, silver nanoparticles have outstanding electrical conductivity, antibacterial property, optical property and catalytic property. The absorption of surface plasmon band of the silver nanoparticles is between 390 nm and 400 nm. The absorption coefficient of the surface thin film of silver nanoparticles is four times more than gold nanoparticles. Therefore, silver nanoparticles applied to an optical sensing system are better than gold nanoparticles.

Figure 2:
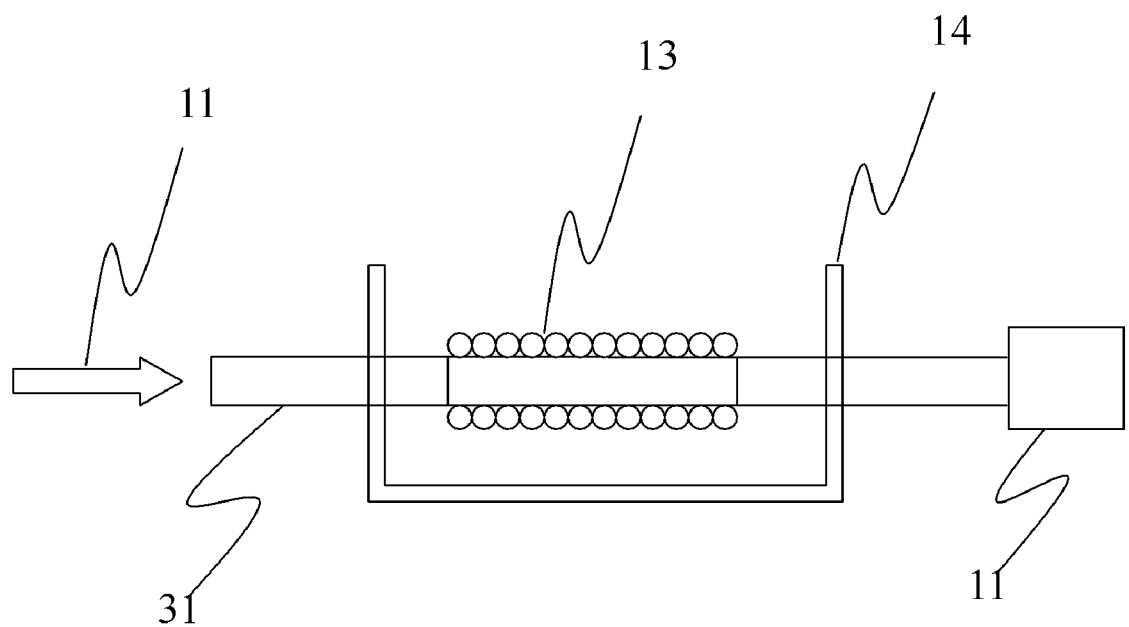
FIG. 2 is a schematic diagram illustrating an optical fiber element taken to be an sensing element of a surface plasmon resonance sensing system of the present invention.

Referring to FIG. 2, a schematic diagram illustrates an optical fiber element taken to be a sensing element in a surface plasmon resonance sensing system of the present invention. The optical fiber element 31 is an optical fiber where a portion of the protection layer and the cladding layer are removed. The noble metal nanoparticle layer 13 is also disposed on the optical fiber element 31. The sample loading unit 14 allows a sample to be contacted with the noble metal nanoparticle layer 13. When the incident light source 11 enters a side of the optical fiber element 31, an emergent light is transmitted from another side of the optical fiber element 31, or exits from the same side of the optical fiber element, or exits from a direction perpendicular to the optical fiber so as to be detected by the light detector 15.

Figure 3:
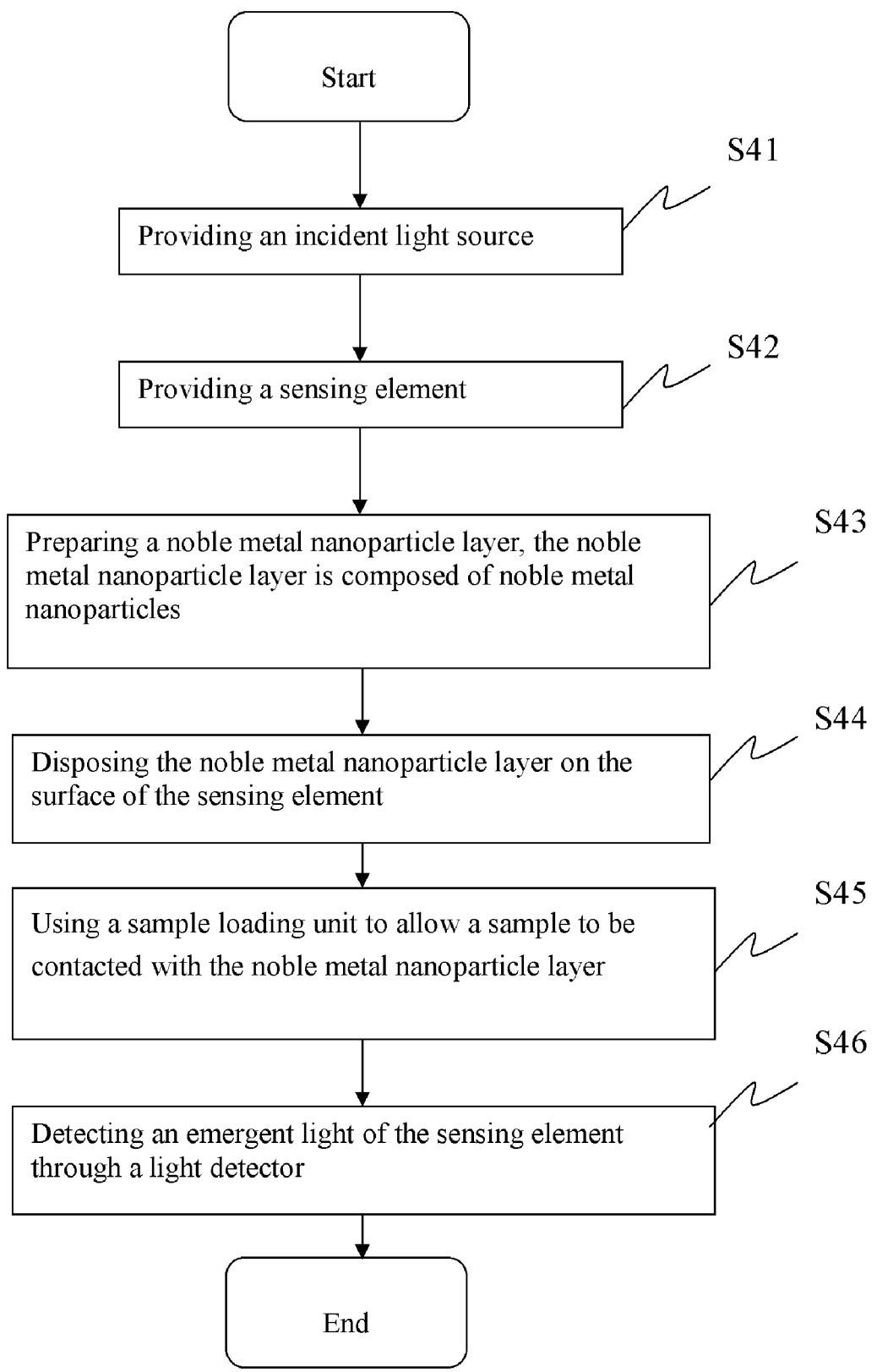
FIG. 3 is a flowchart illustrating a surface plasmon resonance sensing system of the present invention.

Referring to FIG. 3, a flowchart illustrates a surface plasmon resonance sensing method of the present invention. The method comprises the following steps:

Step S41: Providing an incident light source;
Step S42: Providing a sensing element;
Step S43: Preparing a noble metal nanoparticle layer, the noble metal nanoparticle layer is composed of noble metal nanoparticles;
Step S44: Disposing the noble metal nanoparticle layer on the surface of the sensing element;
Step S45: Using a sample loading unit to allow a sample to be contacted with the noble metal nanoparticle layer; and
Step S46: Detecting an emergent light of the sensing element through a light detector.

The noble metal nanoparticle layer is composed of one of noble metal nanospheres, noble metal nanorods and noble metal nanoshells. The noble metal is gold, silver or platinum.

Although the features and advantages of the embodiments according to the preferred invention are disclosed, it is not limited to the embodiments described above, but encompasses any and all modifications and changes within the spirit and scope of the following claims.

What is claimed is:

1. A surface plasmon resonance sensing system comprising:
    an incident light source;
    a sensing element;
    a noble metal nanoparticle layer disposed on a surface of said sensing element; said noble metal nanoparticle layer being composed of noble metal nanoparticles;
    a sample loading unit for allowing a sample to be contacted with said noble metal nanoparticle layer;
    at least one light detector for detecting an emergent light of said sensing element;
    wherein said sensing element is an optical fiber element, and said optical fiber element is an optical fiber where a portion of the protection layer and the cladding layer are removed, and said noble metal nanoparticle layer is disposed on said surface of said optical fiber element;
    wherein said emergent light of said sensing element is a transmitted light, a reflected light, or a leaked light from said optical fiber element or from a planar waveguide plate;
    wherein said emergent light does not include a fluorescence light;
    wherein said noble metal nanoparticle layer absorbs or scatters said incident light and produces said transmitted light, said reflected light, or said leaked light; and
    wherein said surface plasmon resonance sensing system has no polarizer between said incident light source and said sensing element for generating polarized incident light, said surface plasmon resonance sensing system has no optically active medium or polarization rotator between said sensing element and said light detector for rotating a polarization plane of a emergent light from an optical fiber, said surface plasmon resonance sensing system has no spectral filter between said sensing element and said light detector for filtering an excitation light.

2. The surface plasmon resonance sensing system of claim 1, wherein said incident light is a single frequency light, a narrow frequency band light or a white light.

3. The surface plasmon resonance sensing system of claim 1, wherein said noble metal nanoparticle is one of noble metal nanospheres, noble metal nanorods and noble metal nanoshells.

4. The surface plasmon resonance sensing system of claim 1, wherein said noble metal is gold, silver or platinum.

5. A surface plasmon resonance sensing method comprising:
    providing an incident light source;
    providing an optical fiber element to be a sensing element;
    preparing a noble metal nanoparticle layer, said noble metal nanoparticle layer being composed of noble metal nanoparticles;
    disposing said noble metal nanoparticle layer onto the surface of said sensing element;
    using a sample loading unit to allow a sample to be contacted with said noble metal nanoparticle layer;
    detecting an emergent light of said sensing element through a light detector;
    wherein said optical fiber element is produced by removing a portion of the protection layer and the cladding layer from the surface of an optical fiber, and said noble metal nanoparticle layer being disposed onto the surface of said optical fiber element; and
    wherein said surface plasmon resonance sensing system has no polarizer between said incident light source and said sensing element for generating polarized incident light, said surface plasmon resonance sensing system has no optically active medium or polarization rotator between said sensing element and said light detector for rotating a polarization plane of a emergent light from an optical fiber, said surface plasmon resonance sensing system has no spectral filter between said sensing element and said light detector for filtering an excitation light.

6. The surface plasmon resonance sensing method of claim 5, further comprising the step of providing a single frequency light, a narrow frequency band light or a white light to be said incident light.

7. The surface plasmon resonance sensing method of claim 5, further comprising the step of providing one of noble metal nanospheres, noble metal nanorods and noble metal nanoshells to be said noble metal nanoparticles.

8. The surface plasmon resonance sensing method of claim 5, further comprising the step of providing gold, silver or platinum to be said noble metal.

9. The surface plasmon resonance sensing method of claim 5, further comprising the step of providing a transmitted light or a reflected light, or a leaked light from an unclad portion of the optical fiber or from the planar waveguide plate to be said emergent light of said sensing element.

* * * * *